US009398978B2

(12) United States Patent
Lee

(10) Patent No.: US 9,398,978 B2
(45) Date of Patent: Jul. 26, 2016

(54) SYSTEMS AND METHODS FOR REMOVING FIXATION LIGHT REFLECTION FROM AN OPHTHALMIC IMAGE

(71) Applicant: AMO DEVELOPMENT, LLC., Santa Ana, CA (US)

(72) Inventor: Hon M Lee, Ladera Ranch, CA (US)

(73) Assignee: AMO Development, LLC, Santa Ana, CA (US)

( * ) Notice: Subject to any disclaimer, the term of this patent is extended or adjusted under 35 U.S.C. 154(b) by 111 days.

(21) Appl. No.: 13/786,772

(22) Filed: Mar. 6, 2013

(65) Prior Publication Data

US 2014/0257255 A1    Sep. 11, 2014

(51) Int. Cl.
*A61B 3/13* (2006.01)
*A61B 3/14* (2006.01)
*A61F 9/008* (2006.01)
*A61B 3/15* (2006.01)
*A61B 3/00* (2006.01)

(52) U.S. Cl.
CPC . *A61F 9/008* (2013.01); *A61B 3/00* (2013.01); *A61B 3/0008* (2013.01); *A61B 3/0016* (2013.01); *A61B 3/0025* (2013.01); *A61B 3/13* (2013.01); *A61B 3/14* (2013.01); *A61B 3/156* (2013.01); *A61F 9/00802* (2013.01); *A61F 9/00825* (2013.01); *A61F 9/00836* (2013.01); *A61B 3/0091* (2013.01); *A61F 2009/00872* (2013.01); *A61F 2009/00889* (2013.01)

(58) Field of Classification Search
CPC ...... A61B 3/00; A61B 3/0008; A61B 3/0016; A61B 3/0091; A61B 3/10; A61B 3/13; A61B 3/132; A61B 3/135; A61B 3/14; A61B 3/156; A61B 3/15; A61B 18/203; A61B 18/22; A61B 19/5212; A61B 3/0025; A61F 9/008
USPC ................. 351/200, 205, 206, 207, 211, 213; 359/368, 369, 372; 606/4, 5, 6; 604/20, 604/294
See application file for complete search history.

(56) References Cited

U.S. PATENT DOCUMENTS

| 4,589,013 A | * | 5/1986 | Vlahos et al. ................. 348/587 |
| 4,665,913 A | | 5/1987 | L'esperance, Jr. |
| 4,669,466 A | | 6/1987 | L'esperance |
| 4,732,148 A | | 3/1988 | L'esperance, Jr. |
| 4,764,930 A | | 8/1988 | Bille et al. |
| 4,770,172 A | | 9/1988 | L'esperance, Jr. |
| 4,773,414 A | | 9/1988 | L'esperance, Jr. |
| 4,793,654 A | | 12/1988 | Takafuji |
| 5,108,388 A | | 4/1992 | Trokel et al. |
| 5,144,630 A | | 9/1992 | Lin |
| 5,163,934 A | | 11/1992 | Munnerlyn |
| 5,207,668 A | | 5/1993 | L'esperance, Jr. |
| 5,219,343 A | | 6/1993 | L'esperance, Jr. |
| 5,520,679 A | | 5/1996 | Lin |
| 5,646,791 A | | 7/1997 | Glockler |

(Continued)

*Primary Examiner* — Bumsuk Won
*Assistant Examiner* — William R Alexander
(74) *Attorney, Agent, or Firm* — Abbott Medical Optics Inc.

(57) ABSTRACT

Embodiments of the present invention relate to systems and methods for removing the fixation light reflection from an ophthalmic image. In one embodiment, an ophthalmic laser treatment system, having a digital imaging system for capturing images of a patient's eye and a visual fixation light source configured to produce a fixation light upon which the patient's eye can be focused, further includes a filter configured to remove from the image any light reflection caused by the visual fixation light source.

10 Claims, 3 Drawing Sheets

(56) References Cited

U.S. PATENT DOCUMENTS

| | | |
|---|---|---|
| 5,742,626 A | 4/1998 | Mead et al. |
| 5,993,438 A | 11/1999 | Juhasz et al. |
| 6,004,313 A | 12/1999 | Shimmick et al. |
| 6,406,473 B1 | 6/2002 | Shimmick et al. |
| 6,460,997 B1 * | 10/2002 | Frey et al. ............ 351/211 |
| 6,621,917 B1 * | 9/2003 | Vilser .................. 382/128 |
| 6,793,654 B2 | 9/2004 | Lemberg |
| 2009/0275929 A1 * | 11/2009 | Zickler ..................... 606/5 |
| 2012/0188357 A1 * | 7/2012 | Hiramatsu ....... A61B 3/1173 348/78 |

* cited by examiner

SYSTEMS AND METHODS FOR REMOVING FIXATION LIGHT REFLECTION FROM AN OPHTHALMIC IMAGE

FIELD OF THE INVENTION

Embodiments of the present invention generally relate to ophthalmic procedures and, more particularly, to systems and methods for removing fixation light reflection from an ophthalmic image.

BACKGROUND

With recent developments in laser technology and its application in ophthalmology, laser surgery has become the technique of choice for ophthalmic surgery, including refractive surgery for correcting myopia, hyperopia, astigmatism, and the like, and cataract surgery for treating and removing a cataractic lens. Laser eye procedures employ different types of laser beams, such as an ultraviolet laser, an infrared laser, or a near infrared, ultra-short pulsed laser. The surgery is typically performed while the patient is in a reclined position but fully awake. As such, the patient's eye movement has to be stabilized during surgery to ensure the procedure's accuracy and efficacy.

There are various ways to stabilize a patient's eye movement. One approach has the patient focusing on a visual fixation target during the procedure. These targets typically include a light emitting diode (LED), which is optically positioned in front of or above the patient within his or her line of vision. The fixation system generally keeps the LED in focus for the patient even though the optical characteristics of the patient's eye are changing during surgery. Viewing the fixation light targets allows the patient to maintain a steady eye position, thus reducing random eye movement. Exemplary systems and methods for visual fixation are described in U.S. Pat. Nos. 6,004,313 and 6,406,473, issued to Shimmick et al., and U.S. Pat. No. 6,793,654, issued to Lemberg, which are incorporated here by reference in their entirety.

One challenge with contemporary visual fixation systems is that when the surgeon views an image of the patient's eye on a video microscope's LCD display, he or she sees interference in the image caused by light reflections from the fixation system's intervening optics and the cornea. During surgery, surgeons typically rely on the image of the eye captured by a video microscope's LCD display. Light reflection from the visual fixation target, however, often creates a haze in the middle of the displayed image, thereby degrading the quality of the live video feed. This is particularly undesirable for surgeons who depend on a precise image of the eye for the laser treatment.

Hence, improved systems and methods for visual fixation and image display during a laser ophthalmic surgery and/or an ophthalmic diagnostic procedure are desirable.

SUMMARY OF THE INVENTION

Embodiments of this invention relate to systems and methods for removing the fixation light reflection from an ophthalmic image.

In one embodiment, an ophthalmic laser treatment system having a digital imaging system configured to capture an image of a patient's eye and a visual fixation light source configured to produce a fixation light upon which the patient's eye can be focused further includes a filter configured to remove from the image any light reflection caused by the fixation light source.

This summary and the following detailed description are merely exemplary, illustrative, and explanatory, and are not intended to limit, but to provide further explanation of the invention as claimed. Additional features and advantages of the invention will be set forth in the ensuing detailed description and drawings, and in part, will be apparent from the description, or may be learned by practicing various embodiments of the invention. All additional systems, methods, features and advantages are intended to be included within the scope of the invention, and to be protected by the accompanying claims and their equivalents.

BRIEF DESCRIPTION OF THE DRAWINGS

To explain how the above-recited and other advantages and objectives of the inventions are obtained, a more particular description of the embodiments is provided by reference to specific illustrations in the accompanying drawings and as pointed out in the written description and claims. The components in the figures are not necessarily drawn to scale as emphasis is placed on illustrating the general principles schematically rather than literally or precisely. Like reference numerals designate corresponding parts throughout the different views in the figures. But, like parts do not always have like reference numerals.

DETAILED DESCRIPTION OF THE PREFERRED EMBODIMENTS

This disclosure is directed to all applicable variations, changes, and modifications known to those skilled in the art. As such, the following detailed description is merely illustrative and exemplary in nature, and is neither intended to limit the embodiments of the subject matter nor the uses of those embodiments. The terms "exemplary" and "illustrative" mean "serving as an example, an instance, or an illustration." Any implementation described as exemplary or illustrative is not meant to be construed as preferred or advantageous over other implementations. Nor is there any intent to be bound by any expressed or implied theory presented in the background, summary, or the detailed description.

Embodiments of the present invention relate to ophthalmic procedures and, more particularly, to systems and methods for removing the fixation light reflection from an ophthalmic image. For instance, in one embodiment, an ophthalmic laser treatment system, having a digital imaging system configured to capture an image of a patient's eye and a fixation light source configured to produce a fixation light upon which the patient's eye can be focused, further includes a filter configured to remove from the image any light reflection caused by the fixation light source.

Figure 1:
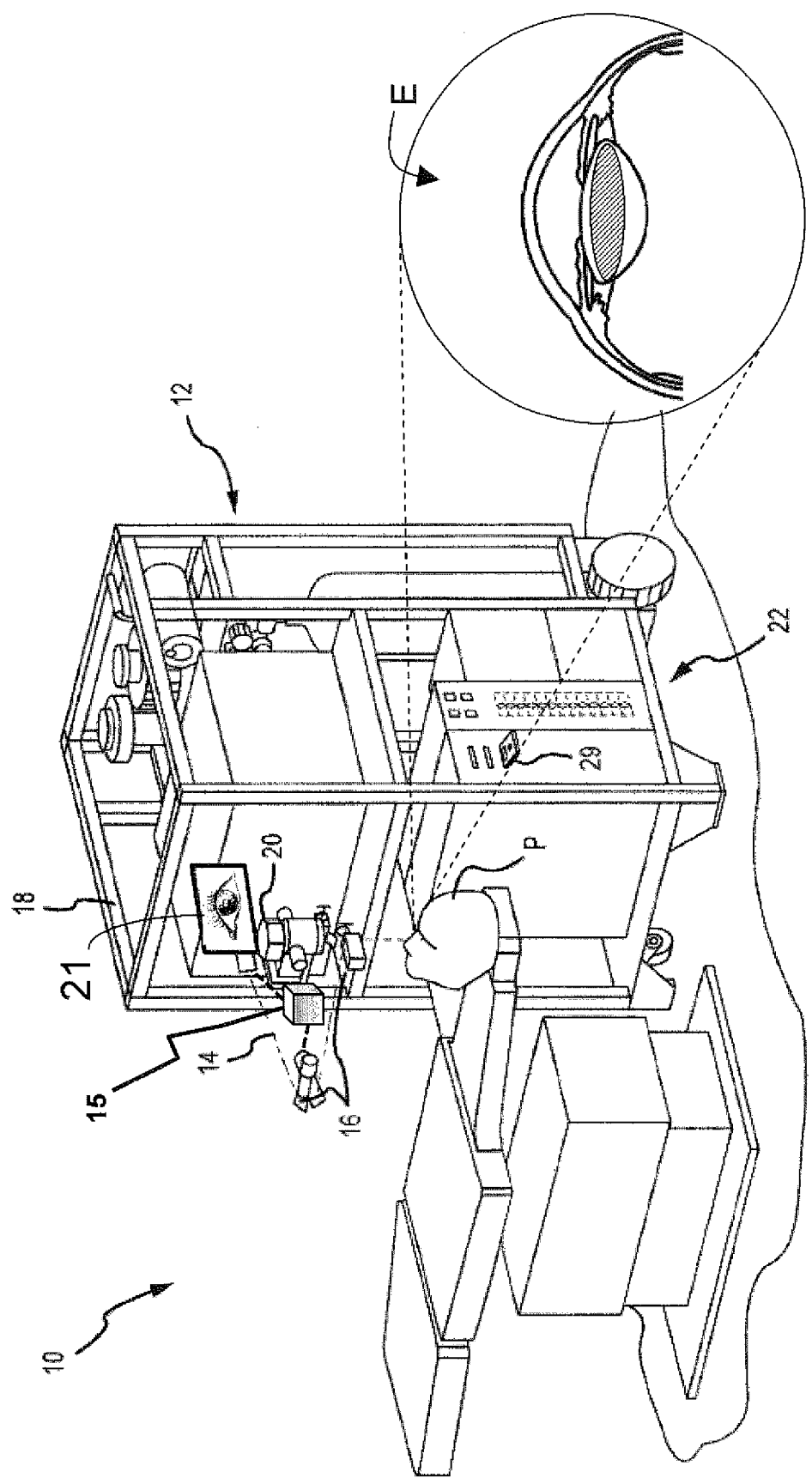
FIG. 1 is a perspective view of a laser eye surgery system according to a preferred embodiment of the present invention.

Turning to FIG. 1, an illustration of a laser-based ophthalmic treatment system 10 according to a preferred embodiment is shown. The laser system 10 includes a laser 12 that produces a laser beam 14. The laser 12 is optically coupled to laser delivery optics 16, which, under the direction of a computer system 22, directs the laser beam 14 to an eye E of patient P. A delivery optics support structure (not shown here for clarity) extends from a frame 18 supporting the laser 12. A microscope 20 is mounted on the delivery optics support structure. The microscope 20 is generally used by the surgeon during a procedure for purposes of guiding the system 10 and for monitoring the patient's eye E. The physician may also use the microscope 20 as a guide when directly engaging the eye E, such as for example, when placing a patient interface on the eye, or when directly treating the eye.

Preferably, microscope 20 is a digital microscope known in the art that uses, among other things, optics and a charged-coupled device ("CCD") camera, to output a digital image to a monitor, such as an LCD display 21. The digital microscope 20 may operate under the direction of the operator and/or the computer system 22.

A visual fixation system 15 is generally coupled to the laser 12, the laser delivery optics 16 and the delivery optics support structure. The visual fixation system 15 includes a light emitting diode (LED), which is optically positioned in front of or above the patient's eye E within the patient's line of vision. The visual fixation system 15 generally keeps the LED targets in focus for the patient even though the optical characteristics of the patient's eye E are changing during surgery. Viewing the fixation light targets allows the patient to maintain a steady eye position, thus reducing and stabilizing random eye movement. The visual fixation system 15 may be manually manipulated by the physician and/or be placed within the control and direction of the computer system 22.

Various devices or systems may be used to generate the pulsed laser beam 14. In one embodiment, system 10 generates a pulsed laser beam 14 with physical characteristics similar to those of the laser beam generated by a laser system disclosed in U.S. Pat. No. 4,764,930 and U.S. Pat. No. 5,993,438, which are incorporated here by reference. For example, system 10 can generate a non-ultraviolet (UV), ultra-short pulsed laser beam 14 having pulse durations that are as long as few nanoseconds and as short as a few femtoseconds. The wavelength of the ultra-short pulsed beam 14 may be in the range of 3 μm to about 1.9 nm, and preferably between about 400 nm to about 3000 nm. Certain non-UV, ultra-short pulsed lasers are used for ophthalmic procedures, including corneal flap-cutting, intrastromal incisions, as well as capsulotomy and other cataract-related procedures. For example, the ophthalmic laser system 10 can produce an ultra-short pulsed laser beam 14 for use as an incising laser beam 14. For intrastromal photodisruption of the tissue, the pulsed laser beam 14 has a wavelength that permits the pulsed laser beam 14 to pass through the cornea without absorption by the corneal tissue. U.S. Pat. No. 5,993,438, which is incorporated here by reference, describes a device for performing ophthalmic surgical procedures to effect high-accuracy corrections of optical aberrations. Among other things, the patent discloses an intrastromal photodisruption technique for reshaping the cornea using a non-UV, ultra-short (e.g., femtosecond pulse duration), pulsed laser beam that propagates through corneal tissue and is focused at a point below the surface of the cornea to photodisrupt stromal tissue at the focal point. Although this embodiment describes a non-ultraviolet, ultra-short pulsed laser beam, other laser systems may be used as a laser source in other embodiments, wherein the laser beam 14 has different pulse durations and wavelengths.

For example, in alternate embodiments, the laser beam source may be an excimer laser comprising an argon-fluorine laser producing pulses of laser light having a wavelength of approximately 193 nm. Alternative laser sources of ultraviolet or infrared radiation may be employed in other embodiments, particularly those adapted to controllably ablate the corneal tissue without causing significant damage to adjacent and/or underlying tissues of the eye. In some embodiments, the laser source may use a solid state laser source with a wavelength between 193 nm and 215 nm, as described in U.S. Pat. Nos. 5,520,679 and 5,144,630, issued to Lin, and U.S. Pat. No. 5,742,626, issued to Mead. The full disclosures of these patents are incorporated here by reference.

Although the laser system 10 may be used to photoalter a variety of materials (e.g., organic, inorganic, or a combination thereof), the laser system 10 is suitable for ophthalmic applications in one embodiment. For instance, the focusing optics could direct the pulsed laser beam 14 toward an eye E (e.g., onto or into a cornea) for plasma mediated (e.g., non-UV) photo-ablation of superficial tissue, or into the stroma of the cornea for intrastromal photodisruption of tissue. In this embodiment, the laser system 10 may also include an interface lens to change the shape (e.g., flatten or curve) of the cornea prior to scanning the pulsed laser beam 14 toward the eye E.

Computer system 22 may comprise (or interface with) a conventional or special computer, e.g., PC, laptop, and so on, including the standard user interface devices such as a keyboard, a mouse, a touch pad, foot pedals, a joystick, a touch screen, an audio input, a display monitor, and the like. Computer system 22 typically includes an input device such as a magnetic or optical disk drive, or an input interface such as a USB connection, a wired and/or wireless network connection, or the like. Such input devices or interfaces are often used to download a computer executable code to a storage media 29, embodying one or more methods of the present invention. Storage media 29 may comprise an optical disk, a data tape, a volatile or non-volatile memory, RAM, or the like, while the computer system 22 includes the memory and other standard components of modern computer systems for storing and executing this code. Storage media 29 includes one or more visual fixation maps, and may optionally include a treatment map, and/or an ablation table. Storage media 29 may alternatively be remotely operatively coupled with computer system 22 via network connections such as LAN, the Internet, or via wireless methods such as WLAN, Bluetooth, or the like.

Additional components and subsystems may be included with laser system 10, as should be understood by those of skill in the art. For example, spatial and/or temporal integrators may be included to control the distribution of energy within the laser beam, as described in U.S. Pat. No. 5,646,791, whose full disclosure is incorporated here by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are incorporated herein by reference.

Figure 2:
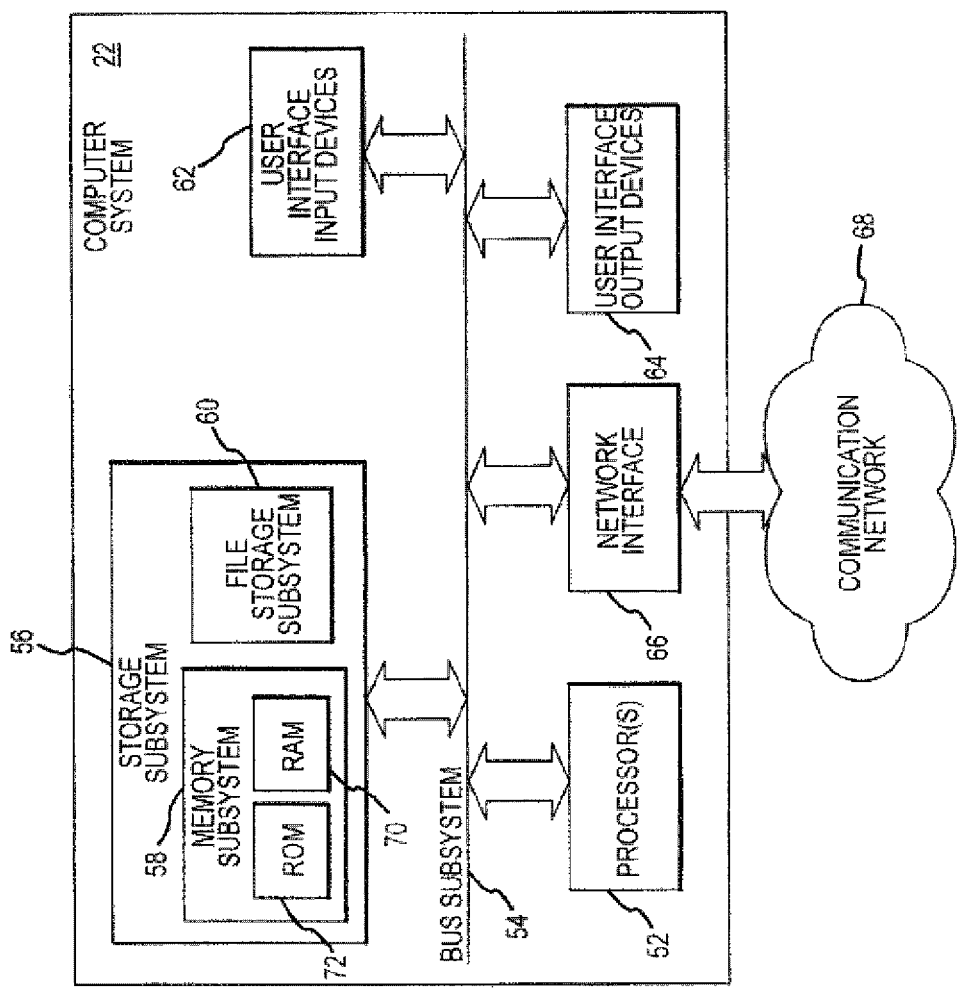
FIG. 2 is a simplified diagram of a computer system according to a preferred embodiment of the present invention.

FIG. 2 is a simplified block diagram of an exemplary computer system 22 that may be used by the laser surgical system 10 of the present invention. Computer system 22 typically includes at least one processor 52 which may communicate with a number of peripheral devices via a bus subsystem 54. These peripheral devices may include a storage subsystem 56, comprising a memory subsystem 58 and a file storage subsystem 60 (which may include storage media 29), user interface input devices 62, user interface output devices 64, and a network interface subsystem 66. Network interface subsystem 66 provides an interface to outside networks 68 and/or other devices.

User interface input devices 62 may include a keyboard; pointing devices such as a mouse, trackball, touch pad, or graphics tablet; a scanner; foot pedals; a joystick; a touch screen incorporated into the display; and/or audio input devices such as voice recognition systems, microphones, and other types of input devices. User interface input devices 62 are often used to download a computer executable code from a storage media 29 embodying one or more methods of the present invention. User interface input devices 62 are also used to control a visual fixation system. In general, use of the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), e.g., LCD display 21 shown in FIG. 1, a projection device, or the like. The display subsystem may also provide a non-visual display such as via audio output devices. In general, use of the term "output device" is intended to include a variety of conventional and proprietary devices and ways to output information from computer system 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include storage media 29 (FIG. 1). File storage subsystem 60 may include a hard disk drive along with associated removable media, a Compact Disk (CD) drive, an optical drive, DVD, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism that allows the various components and subsystems of computer system 22 to communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22, itself, can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as an example for purposes of illustrating one embodiment of this invention. Many other configurations of computer system 22, having more or fewer components than those depicted in FIG. 2, are possible.

Figure 3:
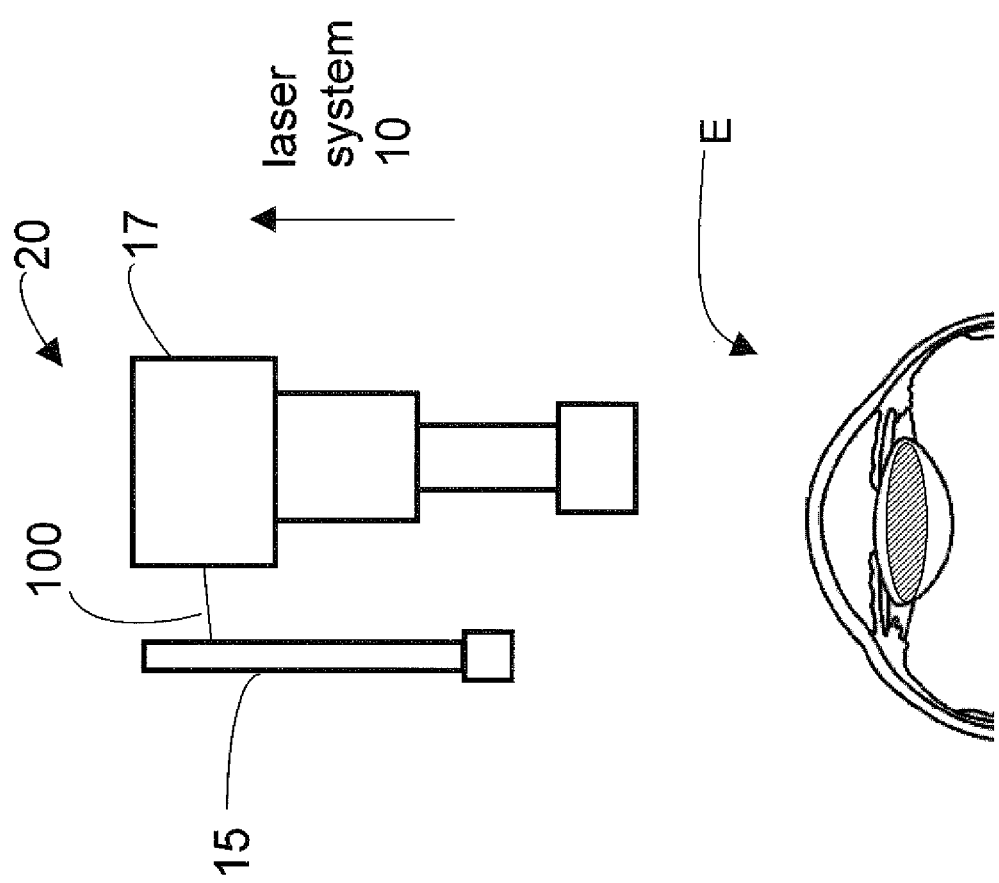
FIG. 3 is a simplified diagram of a digital microscope and a fixation light source according to a preferred embodiment of the present invention.

FIG. 3 shows a more detailed view of the visual fixation system 15 and the digital microscope 20 of laser system 10. As mentioned above, digital microscopes used in laser systems will typically capture the reflection of a fixation light in their images of the eye, thereby obscuring the image. One approach to address this is to remove the light reflection from the image, e.g., the image on LCD display 21, using a filter.

One type of filter is a time-domain filter shown in FIG. 3. As one of ordinary skill in the art will appreciate, digital microscopes capture images in frames displayed to the user sequentially in rapid succession. There is typically a time period in between these frames, known as the inter-frame period, during which the digital microscope 20 is not capturing image data. Generally, the frames and the inter-frame periods are controlled and managed by a controller 17. Further, the controller 17 produces an electric signal indicating the occurrence of an inter-frame period when the digital microscope 20 is not capturing image data. This electric signal can also be referred to as an inter-frame signal. One way of implementing a time-domain filter is by coupling the power of the fixation light 15 to this inter-frame signal in controller 17, using, for example, a switch/connector 100 so that the fixation light 15 synchronizes and turns on only during the inter-frame period. As a result, the fixation light 15 would still be visible to the patient during operation, but would be disabled while the digital microscope 20 is capturing image data. Thus, no light reflection from the fixation light 15 would appear in the image data.

In an alternative configuration, an image filter is used. For instance, computer system 22 may include an image processor and a chroma key component, which is known in the art (not shown). Chroma keying is a technique for compositing two images together based on color hues. One particular objective of this technique is to remove particular objects from an image. In this configuration, after an image is captured with digital microscope 20, the image processor and the chroma key component within computer system 22 digitally remove the fixation light reflection from the captured image.

This disclosure is provided in an exemplary form with a certain degree of particularity, and describes the best mode contemplated of carrying out the invention to enable a person skilled in the art to make and/or use embodiments of the invention. The specific ordering and combination of the processes and structures described are merely illustrative. Those skilled in the art will understand, however, that various modifications, alternative constructions, changes, and variations can be made in the system, method, and parts and steps thereof, without departing from the spirit or scope of the invention. Hence, the disclosure is not intended to be limited to the specific examples and designs that are described. Rather, it should be accorded the broadest scope consistent with the spirit, principles, and novel features disclosed as generally expressed by the following claims and their equivalents.

What is claimed is:

1. An ophthalmic treatment system comprising:
   one or more visual fixation systems configured to produce one or more fixation lights upon which a patient's eye can be focused;
   a digital microscope positioned to capture an image of the patient's eye, wherein the digital microscope capture images in sequential frames with an inter-frame time period between the frames during which the digital microscope does not capture image data;
   a display device operably coupled to the digital microscope to display the image of the patient's eye captured by the digital microscope; and a switch operably coupled to the digital microscope and the one or more visual fixation systems and configured to cause any of the one or more visual fixation systems to produce the visual fixation lights only during the inter-frame periods of the digital microscope, wherein no fixation light enters the patient's eye during time periods when the digital microscope captures the images in the sequential frames.

2. The system of claim 1, wherein the ophthalmic treatment system comprises a laser ophthalmic surgical system having a laser delivery system for delivering a pulsed laser beam to a patient's eye.

3. The system of claim 2, wherein the laser delivery system includes an excimer laser.

4. The system of claim 2, wherein the laser delivery system includes a non-ultraviolet, ultra-short pulsed laser.

5. A method for providing an ophthalmic-based treatment comprising:
   a. capturing an image of a patient's eye with a digital microscope, wherein the digital microscope capture images in sequential frames with an inter-frame time period between the frames during which the digital microscope does not capture image data;
   b. displaying the image on a display device; and
   c. producing visual fixation lights only during the inter-frame periods of the digital microscope, the visual fixation lights being produced in front of the eye to focus the eye at a desired position, wherein no fixation light enters the patient's eye during time periods when the digital microscope captures the images in the sequential frames.

6. The method of claim 5, wherein the ophthalmic-based treatment is laser-based treatment having a laser delivery system for delivering a pulsed laser beam to an eye.

7. The method of claim 6, wherein the laser delivery system includes an excimer laser system.

8. The method of claim 6, wherein the laser delivery system includes a non-ultraviolet ultra-short pulsed laser system.

9. The method of claim 5, wherein the producing step includes using a controller to synchronize power delivered to the visual fixation light to an inter-frame signal so that the visual fixation light turns on only during the inter-frame time periods.

10. The method of claim 9, further including a switch or connector coupled to the visual fixation light which receives the inter-frame signal from the controller and turns on the visual fixation light only during the inter-frame time periods.

* * * * *